Figure 1:
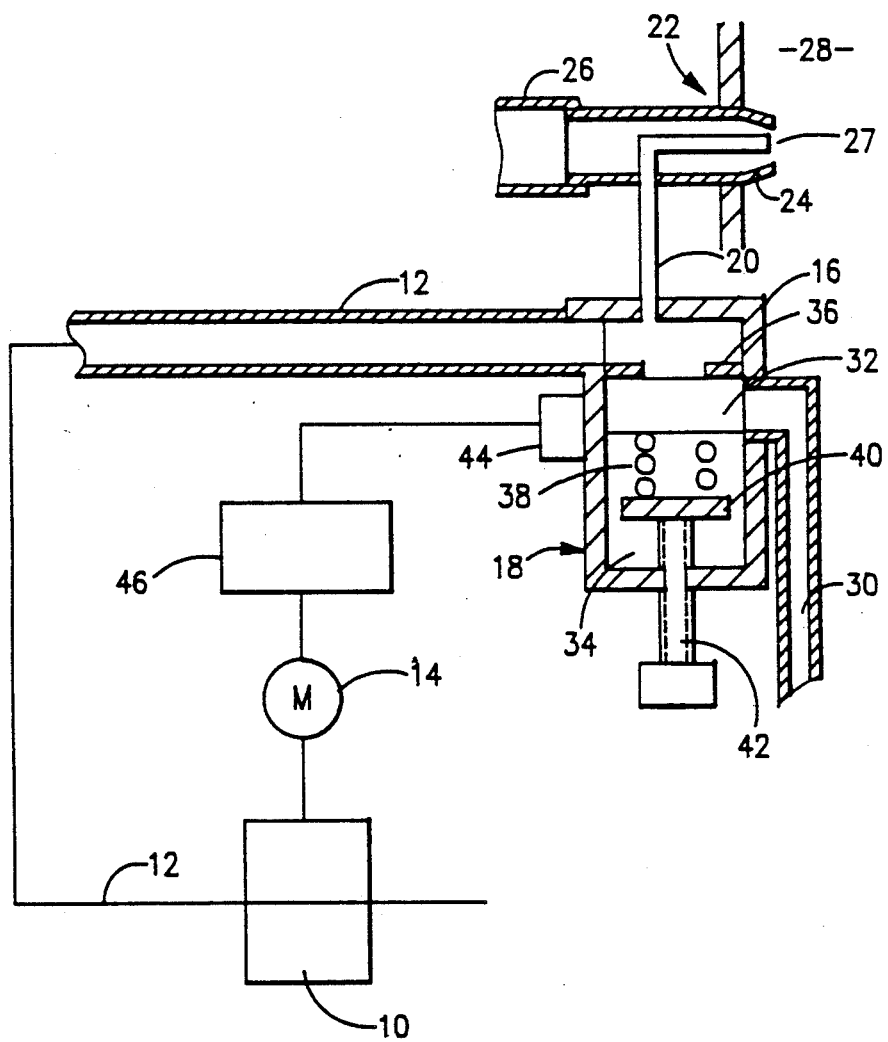

United States Patent [19]

Huber

[11] Patent Number: 4,989,976

[45] Date of Patent: Feb. 5, 1991

[54] DEVICE FOR SUPPLYING LIQUID TO A NEBULIZER IN A SPECTROMETER

[76] Inventor: Bernhard Huber, Hildegardring 42, 7770 Überlingen, Fed. Rep. of Germany

[21] Appl. No.: 355,949

[22] Filed: May 23, 1989

[30] Foreign Application Priority Data

May 27, 1988 [DE] Fed. Rep. of Germany ....... 3818058

[51] Int. Cl.$^5$ ..................... G01N 21/72; G01N 21/73
[52] U.S. Cl. ..................................... 356/315; 356/316
[58] Field of Search ................................ 356/315, 316

[56] References Cited

U.S. PATENT DOCUMENTS 4,322,165 3/1982 Ellebracht et al. ................. 356/316

Primary Examiner—Vincent P. McGraw
Attorney, Agent, or Firm—Thomas P. Murphy; Edwin T. Grimes

[57] ABSTRACT

In a device for supplying liquid to an atomization device operating with a nebulizer (22) in a spectrometer, the liquid is fed to the nebulizer (22) by a peristaltic pump (10) through a supply conduit (12). A valve (18) responding to liquid pressure is arranged closely in front of the nebulizer (22) and controls a connection between the supply conduit (12) and an outlet (30) through which excess liquid can flow off. A sensor (44) responding to the opening of the valve (18) is adapted to control the speed of the peristaltic pump (10), such that the quantity fed by the peristaltic pump (10) is slightly larger than the feeding capacity of the nebulizer (22).

15 Claims, 3 Drawing Sheets

DEVICE FOR SUPPLYING LIQUID TO A NEBULIZER IN A SPECTROMETER

BACKGROUND AND SUMMARY OF THE INVENTION

The invention relates to an atomization device for a spectrometer and more particularly to a device for supplying liquid to an atomization device operating with a nebulizer in a spectrometer.

In spectroscopy techniques for the determination of the concentration of certain elements in a sample liquid, the sample liquid is nebulized by means of a nebulizer in an atomization device. The atomization device can be a flame and the components of the sample are then transformed into an atomic state in this flame. A measuring light beam formed of spectral lines which correspond to the resonant lines of a looked-for element is passed through the flame and is correspondingly specifically attenuated by the atoms of the looked-for element. The attenuation of the measuring light beam therefore provides a measure of the concentration of the looked-for element in the sample. This technique is referred to as atomic absorption spectroscopy operating with a flame, or flame-AAS.

The atomization device can also be a "plasma burner" in which a plasma of a rare gas is provided by inductive excitation and the sample liquid is sprayed into this plasma by a nebulizer. In this high temperature plasma, the atoms of the sample liquid are stimulated so as to emit light The emission lines are characteristic of the respective element and the intensity of the lines provides a measure of the concentration of the element in question in the sample liquid.

The present invention is particularly useful for these and other atomization devices operating with a nebulizer in a spectrometer.

In U.S. Pat. No. 4,486,097, a spectroscopic analytical device is disclosed wherein a sample liquid and alternatively an inert carrier liquid, and a reagent are fed by a peristaltic pump into a common mixer passage. The peristaltic pump is driven by a stepping motor controlled by a microprocessor and the mixed liquids flow into a measuring vessel of a spectrophotometer.

EP No.-A2-0 236 928 discloses the supply of a sample liquid and a reagent to an analytical instrument by means of a peristaltic pump. The analytical instrument may be a photometer with a measuring vessel. The mixture of sample liquid and reagent is directed into the measuring vessel and the photometer responds to a cloudiness or discoloration of the sample liquid caused by a reaction of the sample liquid with the reagent. EP No.-A2-0 236 928 shows arrangements by which a dilution of the sample liquid can be effected through the same peristaltic pump or through a separate peristaltic pump variably driven by a stepping motor in order to keep the concentration of the sample liquid in a favorable range.

EP No.-A2-0 095 291 discloses a device for mixing a sample liquid and a diluting agent (diluent) by means of two peristaltic pumps which each feed into a hose conduit. The hose conduits communicate and terminate in a common conduit which leads to an analytical instrument. The proportion of mixture can be varied.

U.S. Pat. No. 4,315,754 discloses an analytical instrument wherein a carrier liquid and a reagent are pumped into a carrier conduit and into a reagent conduit, respectively, by means of peristaltic pumps. The carrier conduit and the reagent conduit communicate with a mixer conduit which leads to a flow-through detector A change-over valve is located in the carrier conduit and is adapted to optionally connect a loop into the carrier conduit with the loop being arranged to accommodate sample liquid.

In these known arrangements, the mixed liquids are introduced into a vessel or the like and photometrically measured as liquids in the vessel.

In flame-AAS, a sample liquid is sprayed into a flame by a nebulizer and atomized in the flame. The elements of the sample then form an atomic vapor in the flame. The measuring light beam is emitted by a line emitting light source and comprises only light with resonant lines of a looked-for element. The absorption of this measuring light beam is a measure of the concentration of the looked-for element in the sample liquid.

A vacuum is generated in the nebulizer by the effect of the flow of pressurized gas through a nozzle In the area of the vacuum, sample liquid is aspirated from a sample vessel through a capillary. Due to the differences of the flow speeds of the emerging pressurized gas and the aspirated sample liquid, the sample liquid is torn to fine drops A sample mist results in the mixer chamber which is taken along into the flame by fuel gas flow introduced into the mixer chamber (DE-B-No. 22 04 938, U.S. Pat. No. 3,525,476, DE-No. A1-35 31 276, DE-No. A1-30 26 155). Such nebulizers have a limited feed capacity and can aspirate and nebulize only a certain quantity of liquid per unit time.

In known plasma burners, a rare gas plasma having very high temperatures is generated by high frequency. The sample liquid is introduced into this plasma and thereby atomized The sample atoms are stimulated to emission of light in the plasma and the emission spectrum is observed and evaluated (Welz "Atomabsorptions—Spektroskopie" 3 edition (1983) Publishers Chemie, 271). This measuring method permits the simultaneous measurement of different elements in contrast to atomic absorption spectroscopy.

It is known to introduce the sample liquid as an aerosol into the plasma burner (Welz loc cit) and to form this aerosol by means of a nebulizer (Doherty and Hieftje in "Applied Spectroscopy" vol. 38 (1984), 405–4121).

It has been tried to direct the sample liquid to the nebulizer by means of a peristaltic pump. However, this makes it necessary to adapt the feed output of the peristaltic pump to the limited feed output of the nebulizer or otherwise a "jam" would result. Furthermore, problems arise when changing sample. With the low feed capacity of a nebulizer, it takes a long time for the remainder of sample present in the hose to be aspirated through the nebulizer and atomized, and the hose to be rinsed It is an object of the present invention to provide a new and improved device for supplying liquid to a nebulizer in a spectrometer.

Another object of the invention is to provide a device for supplying liquid with a peristaltic pump to a pneumatic nebulizer which prevents a feed jam at the nebulizer and which does not necessitate adapting the feed output of the peristaltic pump to the nebulizer output.

A further object of the invention is to provide such a device which attains rapid rinsing of nebulizer feed conduits when changing sample.

A further object of the invention is to provide such a device which has widespread application in a number of spectroscopic configurations.

Other objects will be in part obvious and in part pointed out more in detail hereinafter.

It has been found that the foregoing and related objects may be achieved in a combination of an atomization apparatus and nebulizer supplied by a peristaltic pump. The peristaltic pump supplies liquid feed to the nebulizer through a supply conduit. A discharge valve is mounted in the supply conduit for automatically discharging liquid feed in excess of the input feed capacity of the nebulizer.

The discharge valve responds to liquid pressure and is positioned closely in front of the nebulizer. The discharge valve controls a connection between the supply conduit and an outlet through which excess liquid can be discharged off. With such an arrangement, the feed output of the peristaltic pump can be chosen to any extent. The nebulizer always takes up a quantity of fluid corresponding to its feed capacity and atomizes it. The excess fluid flows off through the valve outlet. This makes it possible to generate a strong flow of rinsing liquid or sample liquid of the next sample after a sample change by which flow the hose is quickly rinsed up to the valve. Consequently, just the small space between the valve and nebulizer capillary has to be rinsed through the nebulizer. Thus, the combination of a peristaltic pump with an atomization device operating with a nebulizer is beneficially usable. This, in turn, makes it possible to use the different methods of operation with peristaltic pumps (as described above partly as prior art) in connection with such an atomization device.

It is particularly advantageous when a sensor responding to the opening of the valve is adapted to control the speed of the peristaltic pump. With such control, the wasting of liquid, particularly sample liquid, is counteracted. The peristaltic pump is controlled to feed only so much liquid that the valve just opens. Then the major portion of this liquid is aspirated by the nebulizer and just a small portion discharges off through the valve.

In another embodiment of the invention, a first and a second peristaltic pump are arranged to be optionally connected to the nebulizer, and the valve sensor is adapted to control the speed of the peristaltic pump presently connected to the nebulizer. This permits an alternating measurement with sample liquid and standard (neutral solution).

In a further embodiment, a first and second peristaltic pump are connected in parallel to the nebulizer and the valve sensor is adapted to control the speeds of the first and second peristaltic pumps such that the sum of the feed rate of the two pumps is kept at a value slightly above the feed capacity of the nebulizer. Such an arrangement permits, for example, the production of different dilutions.

Furthermore, the feed capacity of the peristaltic pumps can be adapted to be increased to a value considerably exceeding the feed capacity of the nebulizer for rapid rinsing purposes when changing sample.

BRIEF DESCRIPTION OF THE DRAWINGS

FIG. 1 is a schematic view of a nebulizing nozzle and the device of the present invention for supplying liquid thereto.

FIG. 2 is a schematic view of a flow injection configuration embodying the present invention with a measuring loop containing sample liquid to be supplied to the nebulizer of an atomization burner and arranged to be selectively connected into the carrier liquid flow.

FIG. 3 shows the arrangement of FIG. 2 after the measuring loop has been connected into the carrier liquid flow.

FIG. 4 is a schematic view of an arrangement for automatic dilution of a sample liquid supplied to the nebulizer of a burner in an atomic absorption spectrometer with the dilution being automatically controlled to obtain an optimum signal.

FIG. 5 is a schematic view of a configuration for optimal supply of sample or standard to a nebulizer in the mode for supplying sample.

FIG. 6 shows the arrangement of FIG. 5 in the alternate mode for supplying standard to the nebulizer.

DESCRIPTION OF THE PREFERRED EMBODIMENT

Although specific forms of the present invention have been selected for illustration in the drawings, and the following description is drawn in specific terms for the purpose of describing these forms of the invention, the description is not intended to limit the scope of the invention which is defined in the appended claims.

Referring to the drawings wherein the same numerals are used to identify like or similar parts throughout the several figures, the numeral 10 in FIG. 1 designates a peristaltic pump which is driven by a stepping motor 14 and is arranged to feed a liquid, for example a sample liquid, into a hose conduit 12. The hose conduit 12 leads to the valve housing 16 of valve 18. A capillary 20 extends from the valve housing 16 to a nebulizer 22.

The nebulizer 22 comprises a nozzle 24 connected to a pressurized air supply conduit 26. The pressurized air emerges at high speed through the nozzle and expands thereby to produce a vacuum. The capillary 20 ends in the region 27 of this vacuum so that the vacuum aspirates liquid from the hose conduit 12 and the valve housing 16. As a result of the difference of the speeds of the liquid and the pressurized air, the liquid is torn into fine drops and forms an aerosol with the pressurized air. The aerosol is guided into a mixer chamber 28 of a burner. In the mixer chamber, the aerosol is mixed in a known way with a fuel gas and taken along by this fuel gas to the burner head. This is a prior art technique and need not be described in further detail herein.

The valve 18 is positioned immediately upstream from the nebulizer 22 being connected to the nebulizer nozzle 24 by the small capillary 20. The valve 18 responds to the pressure of the liquid in the hose conduit 12 and valve housing 16 so as to control an outlet 30 through which excess liquid is discharged into a waste vessel (not illustrated). To this end, the valve 18 has a piston 32 mounted for reciprocal movement in the cylinder 34 formed by valve housing 16. The outlet 30 extends laterally from the cylinder 34. The upward stroke of the piston 32 toward the hose conduit 12 and the capillary 20 is limited by a stop ring 36. The piston 32 is biased by a helical spring 38 supported on a spring abutment 40. The spring abutment 40 is adjustable by means of a screw 42 so the bias of the helical spring 38 can be regulated and thus the pressure of the liquid at which the valve 18 opens is selectable. When the piston 32 engages the stop ring 36, the outlet 30 is covered by the piston 32 and thus the valve 18 is closed.

A sensor 44 is adapted to sense the stroke of the piston 32 and respond to the opening of the valve 18.

Through a control device 46, the sensor 44 controls the stepping motor 14. The speed of the stepping motor 14 is controlled by the control device 46 so that the valve 18 is just slightly open.

In operation, the nebulizer 22 aspirates a determined maximum liquid quantity per unit time even if the pressure in the hose conduit 12 increases. The feed quantity of the peristaltic pump 10 is adapted to the feed capacity of the nebulizer 22 by the valve 18 in order to avoid a "jam". The valve 18 opens responsive to pressure and discharges liquid not aspirated by the nebulizer 22 through the outlet 30 so as to prevent jamming. In order to limit the consumption of liquid, the peristaltic pump 10 is controlled by the sensor 44 through the control device 46. The control device 46 is arranged so that when the valve 18 opens too wide, the speed of the peristaltic pump 10 is reduced so that the major portion of the liquid feed is aspirated by the nebulizer 22 and only a small amount discharges through the outlet and is lost.

Figure 2:
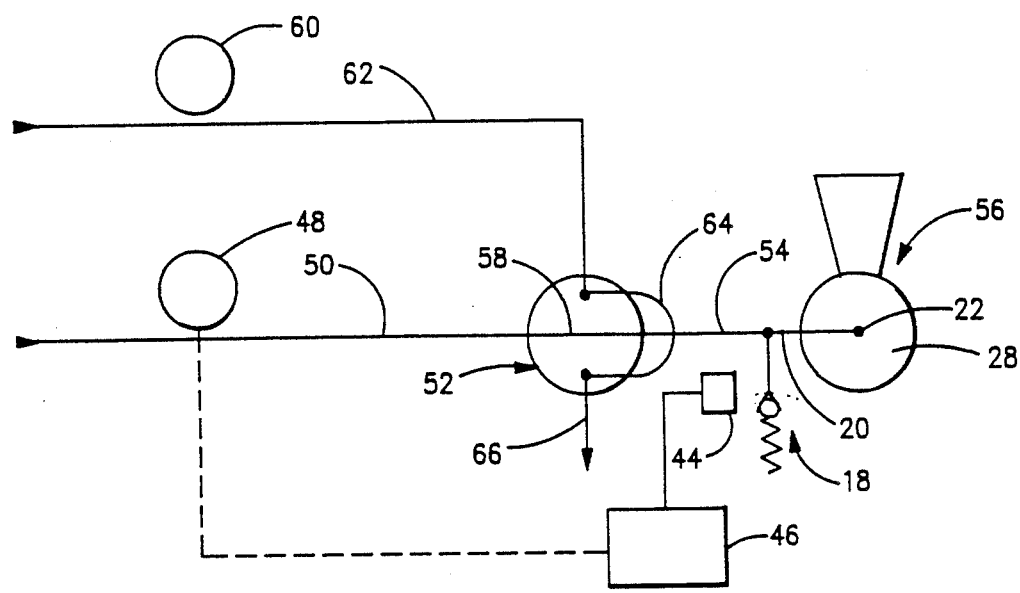
Figure 3:
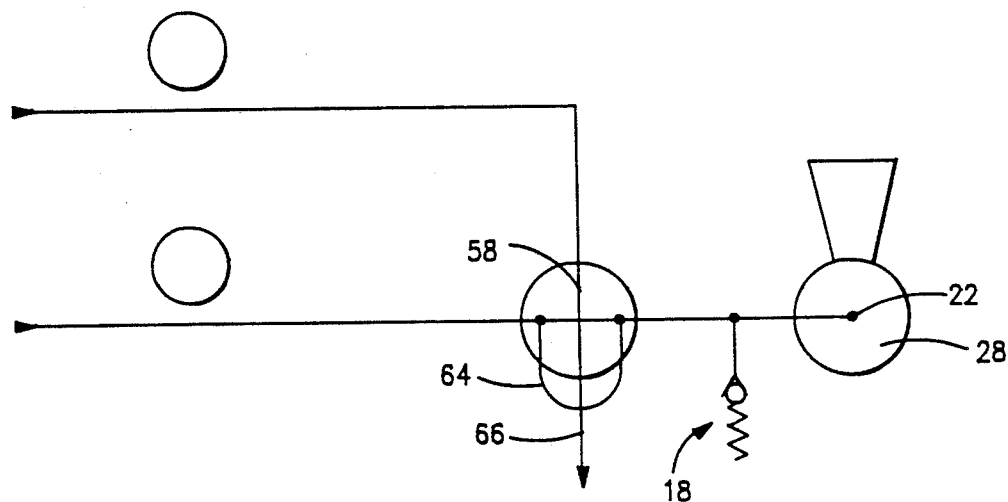

Referring to FIGS. 2 and 3, a flow injection configuration utilizing the liquid supply device of the present invention is shown in alternate operating positions A flow of carrier liquid is fed by a peristaltic pump 48 through the hose conduit 50. The hose conduit 50 is connected through a change-over valve 52 to a conduit 54 which is connected to the nebulizer 22 of burner 56. The valve 18 is positioned closely or immediately before (i.e., upstream) the capillary 20 leading to the nebulizer 22. The conduit 54 corresponds approximately to the conduit 12 in the arrangement of FIG. 1 with the valve 18 and nebulizer 22 being similarly configured.

The change over valve 52 has a passage 58 interconnecting the hose conduit 50 and the conduit 54 in the position of FIG. 2. A further peristaltic pump 60 feeds sample liquid into the hose conduit 62 which is interconnected to the waste outlet 66 through the change-over valve 52 and the measuring loop 64.

In the position of FIG. 2, the nebulizer 22 receives pure carrier liquid while the measuring loop 64 is filled with sample liquid by the peristaltic pump 60. After the change-over valve has been moved into the position of FIG. 3, the measuring loop 64 filled with sample liquid is thus connected into the flow of the carrier liquid and the hose conduit 62, also containing sample liquid, is connected to the waste outlet 66 through the passage 58. The sample liquid contained in the measuring loop 64 is then transported into the nebulizer 22 by the flow of the carrier liquid.

The signal of the sensor 44 is applied to the control device 46. The control device 46 controls the speed of the peristaltic pump 48 as a function of the signal from the sensor 44, and pump 48 feeds liquid (carrier liquid or sample liquid) to the nebulizer 22.

Figure 4:
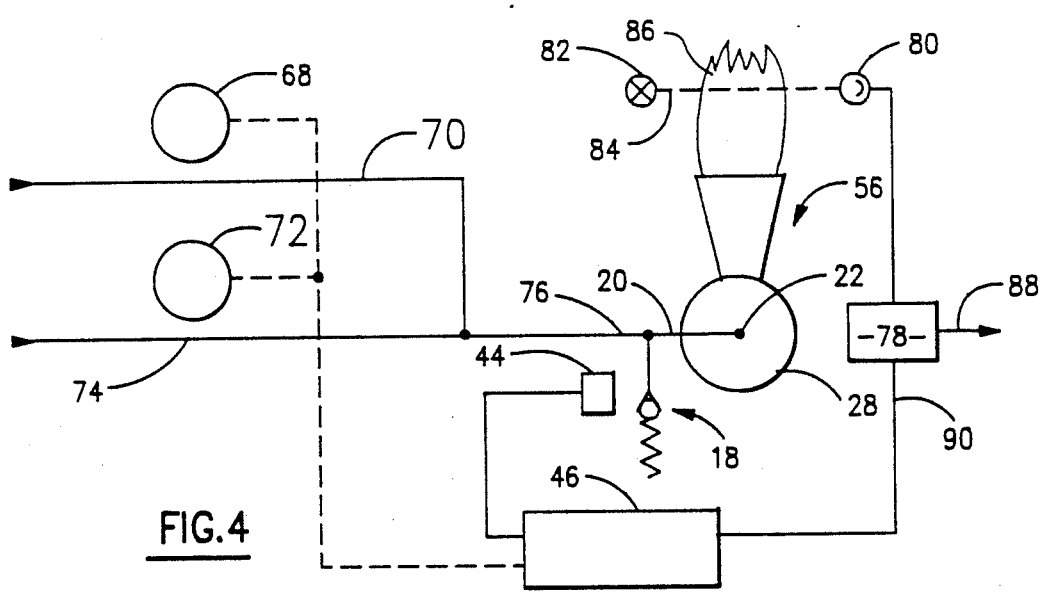

In the automatic dilution configuration of FIG. 4, the peristaltic pump 68 is connected to feed a sample liquid into the sample hose conduit 70. A peristaltic pump 72 is connected to feed a dilution liquid into the dilution hose conduit 74. The sample conduit 70 and the dilution conduit 74 are connected to form a mixer conduit 76. The mixer conduit 76 is connected to the valve 18 and the nebulizer 22 of burner 56 via the capillary 20 similar to FIG. 1 with the mixer conduit 76 corresponding to the hose conduit 12.

The speeds of the peristaltic pumps 68 and 72 are controlled by the control device 46. The control device 46 receives a signal from the sensor 44 and a signal from the signal evaluation circuit 78. A line emitting light source 82 directs a measuring light beam 84 through the flame 86 of burner 56. This measuring light beam 84 impinges upon the photodetector 80 and the photodetector signal is applied to the signal evaluation circuit The measuring light beam 84 is attenuated as a function of the concentration of the looked-for element in the sample liquid. Correspondingly, the signal of the photodetector is dependent on this concentration and based upon this signal, the signal evaluation circuit 78 provides a measuring value of the concentration of the looked-for element in the sample liquid. The output from this measuring value is identified as output 88. This is the known principle of atomic absorption spectroscopy and therefore need not be described in detail.

For an atomic absorption measurement, a certain concentration range is optimal in each case. If the concentration of the looked-for element in the liquid supplied to the nebulizer is too low, as for example when the sample liquid is diluted too much by dilution liquid, then the sensitivity will be too low. There will not be enough atoms of the looked-for element in the flame and the low absorption of the measuring light beam will be submerged in the background absorption and background noise. If the concentration of the looked-for element is too high in the liquid supplied to the nebulizer, then the measuring light beam will be absorbed virtually completely such that an exact concentration measurement also cannot be made. When practically the total light of the measuring light beam is absorbed, then even doubling the concentration of the looked-for element would not cause any substantial change of the signal at the photodetector 80. An optimum concentration is located between these extremes whereby the concentration can be measured with high accuracy.

By controlling the speeds and thus the feed capacities of the two peristaltic pumps 68 and 72, the dilution of the sample liquid with dilution liquid can be varied in a well-defined way so as to attain optimum sensitivity. To this end, the ratio of the feed capacities of the two peristaltic pumps 68 and 72 is controlled by the control device 46 as a function of an output signal at output 90 of the signal evaluation circuit 78 such that the measuring light beam 84 is subjected to optimum mean absorption in the flame 86. If the absorption is too high, the speed of the peristaltic pump 72 is increased and the speed of the peristaltic pump 68 is reduced. If the absorption is too low, then the speed of the peristaltic pump 68 is increased and the speed of the peristaltic pump 72 is reduced.

The control device 46 controls the speeds of the two peristaltic pumps 68, 72 also as a function of the signal of the sensor 44 at the valve 18. The speeds are controlled such that the sum of the feed quantities of the two peristaltic pumps 68 and 72 is slightly larger than the feed capacity of the nebulizer 22.

Figure 5:
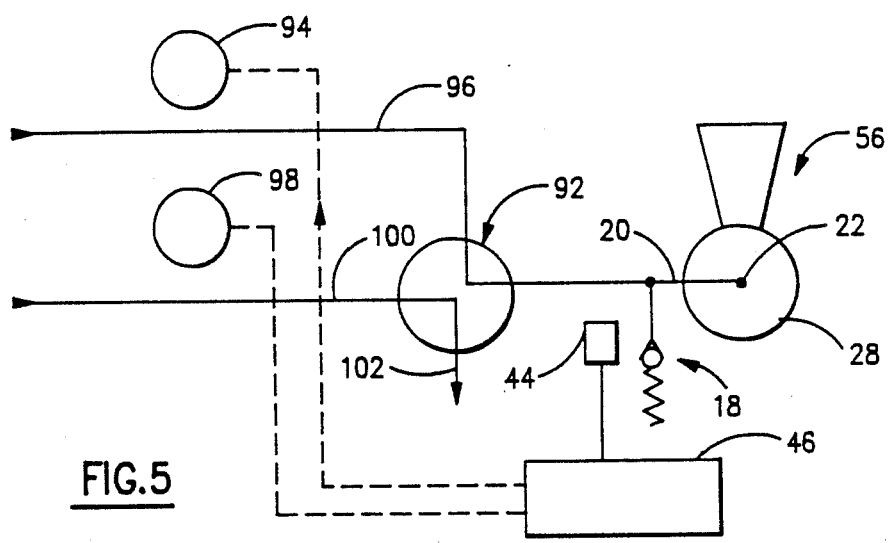
Figure 6:
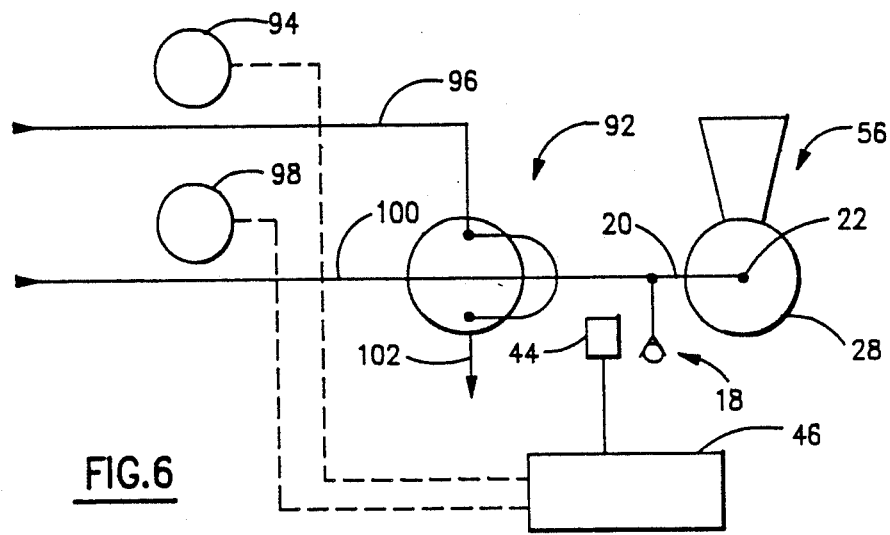

In FIGS. 5 and 6, a further configuration of the present invention is shown for alternately supplying either a sample liquid or a standard (such as a neutral solution) to the nebulizer 22 Through the change-over valve 92, sample liquid can be supplied to the nebulizer 22 through a conduit 96 by peristaltic pump 94, or a standard can be supplied to nebulizer 22 through conduit 100 by peristaltic pump 98. In FIG. 5, the change-over volume 92 is shown in a first position wherein the conduit 96 is connected through the change-over valve 92 to the nebulizer 22 and valve 18, and the conduit 100 is connected through the change-over valve 92 to a waste outlet 102. In FIG. 6, the change-over valve is shown in a second position wherein the conduit 100 is connected through the change-over valve 92 to the nebulizer 22 and valve 18, and the conduit 96 is connected to the waste outlet 102. Thus, absorption can alternately be measured with sample liquid or with the standard.

In both positions of the change-over valve 92, the respective peristaltic pump 94 or 98 then connected to the nebulizer is controlled by the control device 46 so that the feed quantity is slightly larger than the feed capacity of the nebulizer. As indicated by arrows at the broken line connections, the control device 46 controls the peristaltic pump 94 in FIG. 5 and the peristaltic pump 98 in FIG. 6.

For the purpose of rinsing the peristaltic pumps, all of the illustrated embodiments permit change-over to a substantially increased feed quantity of rinsing liquid or sample liquid of the next sample to be aspirated. The increased feed quantity then flows off through the valve 18 and the discharge outlet 30 so that the conduits are rinsed independently of the feed capacity of the nebulizer 22. Consequently, the nebulizer 22 need only feed or aspirate the small liquid quantity necessary for rinsing the capillary 20. Accordingly, a quick sample change can be accomplished.

As can be seen, a device for supplying liquid to a pneumatic nebulizer with a peristaltic pump has been described which prevents a feed jam at the nebulizer without the necessity of adapting the output of the peristaltic pump to the input feed rate of the nebulizer. Moreover, the device attains rapid rinsing of the feed conduits when changing sample and can be utilized in a wide variety of spectroscopic configurations.

As will be apparent to persons skilled in the art, various modifications and adaptations of the structure above described will become readily apparent without departure from the spirit and scope of the invention, the scope of which is defined in the appended claims.

What is claimed is:

1. In combination,
   atomization means for transforming sample into an atomic state for spectroscopic analysis,
   nebulizer means for nebulizing liquid for introduction into said atomization means, said nebulizer means being connected to said atomization means,
   supply conduit means for conducting liquid to be nebulized to said nebulizer means,
   peristaltic pump means for supplying liquid through said conduit means to said nebulizer means,
   said nebulizer means having a predetermined liquid input feed rate,
   discharge valve means for automatically discharging liquid feed to said nebulizer in excess of said predetermined input feed rate so as to prevent liquid feed jamming at said nebulizer, said valve means being connected to said supply conduit means and having a discharge outlet, and
   discharge conduit means connected to the outlet of said valve means for discharging excess liquid.

2. The device of claim 1 comprising
   sensor means for sensing the discharge of liquid feed from said valve means and
   control means for controlling said pump means based upon the discharge of liquid feed from said valve means, said control means being connected to said sensor means.

3. The device of claim 2 wherein said control means is configured for selectively controlling said pump means so that the feed supply of liquid to said nebulizer means is slightly above said predetermined input feed rate of said nebulizer means for spectroscopic analysis.

4. The device of claim 3 wherein said control means is configured for selectively controlling said pump means so that the feed supply of liquid to said nebulizer sufficiently, exceeds said predetermined input feed rate of said nebulizer means for rapid rinsing of said valve means and said supply conduit means when changing the liquid to be fed to said nebulizer means.

5. The device of claim 1 which comprises
   said valve means comprising a pressure actuated discharge control valve for controlling the amount of discharge through said discharge conduit means,
   sensor means for sensing position of said control valve, and
   means for controlling said peristaltic pump means responsive to said control valve, said controlling means being connected to said sensor means.

6. The device of claim 5 wherein
   said peristaltic pump means has a pumping feed capacity considerably greater than said liquid input feed rate of said nebulizer means, and
   said control means includes means for controlling the speed of said peristaltic pump means for alternately supplying liquid to said nebulizer means slightly above said predetermined input feed rate of said nebulizer means and alternately substantially exceeding said input feed rate.

7. The device of claim 5 wherein
   said control valve has a piston movably mounted for closing off said discharge outlet and
   said sensing means comprises means for sensing the position of said piston.

8. The device of claim 1 which comprises
   said valve means comprising a pressure actuated discharge control valve, said control valve being connected immediately adjoining said nebulizer means,
   sensor means for sensing the opening of said control valve, and
   means for controlling the speed of said peristaltic pump means responsive to said control valve, said controlling means being connected to said sensor means.

9. The device of claim 8 wherein
   said peristaltic pump means comprises first and second peristaltic pumps configured for selective alternate connection to said nebulizer means and
   said control means is configured to control said first and second peristaltic pump when connected to said nebulizer means.

10. The device of claim 9 wherein
    said first and second peristaltic pumps each have feed capacities considerably exceeding the predetermined input feed rate of said nebulizer means for rinsing operations.

11. The device of claim 8 wherein
    said peristaltic pump means comprises first and second peristaltic pumps connected in parallel to said nebulizer means and
    said control means is configured to control said first and second peristaltic pump such that the combined feed quantities of said first and second pump is at a value slightly above said predetermined input feed rate of said nebulizer means.

12. The device of claim 11 wherein
    said first and second peristaltic pumps each have feed capacities considerably exceeding the predetermined input feed rate of said nebulizer means for rinsing operations.

13. The device of claim 8 which comprises said peristaltic pump means comprising first and second peristaltic pumps, said first peristaltic pump being configured to feed carrier solution to said nebulizer means through a carrier conduit, said second peristaltic pump being configured to feed sample liquid into a sample conduit, a measuring loop, a change-over valve means for alternately connecting said measuring loop to said sample conduit and said carrier conduit, said change-over valve means having first and second positions with said measuring loop being connected to said sample conduit and a discharge waste and said carrier conduit being connected to said nebulizer means in said first position and said measuring loop being interconnected between said carrier conduit and said nebulizer means and said sample conduit being connected to said discharge waste in said second position.

14. The device of claim 8 which comprises said peristaltic pump means comprising first and second variable speed peristaltic pumps, a sample conduit, said first peristaltic pump being configured to feed sample liquid through said sample conduit, a dilution conduit, said second peristaltic pump being configured to feed dilution liquid through said dilution conduit, a mixer conduit connected to said sample conduit and said dilution conduit for receiving sample liquid and dilution liquid and to said nebulizer for conducting liquid thereto, and said control means being adapted for varying the speeds of said first and second pumps to vary the dilution of sample liquid being fed to said nebulizer means.

15. The device of claim 8 which comprises a sample liquid conduit a standard liquid conduit, said peristaltic pump means comprising first and second peristaltic pumps with said first pump being adapted to feed sample liquid through said sample conduit and said second pump being adapted to feed standard liquid through said standard conduit and a change-over valve for alternately connecting said sample and standard conduits to said nebulizer means and a waste outlet, said change-over valve having first and second positions with said sample conduit being connected to said nebulizer means and said standard conduit being connected to said waste outlet in said first position and said standard conduit being connected to said nebulizer means and said sample conduit being connected to said waste outlet in said second position.

* * * * *